United States Patent [19]

Macfarlane

[11] Patent Number: 5,300,635
[45] Date of Patent: Apr. 5, 1994

[54] QUATERNARY AMINE SURFACTANTS AND METHODS OF USING SAME IN ISOLATION OF NUCLEIC ACIDS

[75] Inventor: Donald E. Macfarlane, Iowa City, Iowa

[73] Assignee: University of Iowa Research Foundation, Iowa City, Iowa

[21] Appl. No.: 13,419

[22] Filed: Feb. 1, 1993

[51] Int. Cl.$^5$ ............................................. C07H 21/00
[52] U.S. Cl. .................................... 536/25.4; 564/281
[58] Field of Search ................ 536/25.4, 281; 564/281

[56] References Cited

U.S. PATENT DOCUMENTS 4,843,155  6/1989  Chomczynski ..................... 536/27
5,010,183  4/1991  Macfarlane ........................ 536/27

OTHER PUBLICATIONS

Seibert, G. et al. The Separation of High and Low Molecular Weight RNA by Precipitation . . . , Z., Naturforsch Sect C Biosciences (1977) 32: 294–296.

Chomczynski, P. et al. Single-Step Method of RNA Isolation by Acid Quanidium . . . Anal. Biochem (1987) 162:156–159.

Chirgwin et al, "Isolation of Biologically Active Ribonucleic Acid from Sources Enriched in Ribonuclease", *Biochem.*, 18(24):5294–5299 (1979).

D. M. Wallace, "Large- and Small-Scale Phenol Extractions", *Meth. Enzym.*, 152:33–41 (1987).

T. Maniatis et al, *Molecular Cloning, A Laboratory Manual*, Cold Spring Harbor Laboratory (1982).

L. G. Davis et al, "Guanidine Isothiocyanate Preparation of Total RNA" and RNA Preparation: Mini Method in *Basic Methods in Molecular Biology*, Elsevier, New York, pp. 130–138 (1991).

R. Kingston et al, "Preparation and Analysis of RNA" in *Current Protocols in Molecular Biology*, Unit 4.2 (Supplement 14), ed. F. M. Ausubel et al, John Wiley, (1991).

*Primary Examiner*—Margaret Parr
*Assistant Examiner*—David Schreiber
*Attorney, Agent, or Firm*—Howson and Howson

[57] ABSTRACT

The present invention discloses a novel method for isolating nucleic acids from biological samples, most particularly blood, using selected quaternary amine surfactants. The nucleic acids are isolated quickly and in sufficient quantity and quality to permit analysis by methods including reverse transcriptase and polymerase chain reaction.

15 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:1:

TCAGACCCTG AGGCTCAAAG TC      22

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:2:

GAAGCTTCTC CCTGGCATCC GT      22

QUATERNARY AMINE SURFACTANTS AND METHODS OF USING SAME IN ISOLATION OF NUCLEIC ACIDS

FIELD OF THE INVENTION

This invention relates generally to the isolation of ribonucleic acids from blood and other biological samples, and more specifically to a method of isolation employing novel quaternary amine surfactants.

BACKGROUND OF THE INVENTION

Research in the field of molecular biology has revealed that the genetic origin and functional activity of a cell can be deduced from the study of its ribonucleic acid (RNA). This information may be of use in clinical practice, to diagnose infections, to detect the presence of cells expressing oncogenes, to detect familial disorders, to monitor the state of host defense mechanisms and to determine the HLA type or other marker of identity.

Current methods for isolating RNA include a variety of techniques to disrupt the cell and liberate RNA into solution and to protect RNA from RNases. Thereafter, the RNA is separated from the DNA and protein which is solubilized along with the RNA. The use of the powerfully chaotropic salts of guanidinium to simultaneously lyse cells, solubilize RNA and inhibit RNases was described in Chirgwin et al, *Biochem.*, 18:5294–5299 (1979). Other methods free solubilized RNA of contaminating protein and DNA by extraction with phenol at an acidic pH using chloroform to effect a phase separation [D. M. Wallace, *Meth. Enzym.*, 152:33–41 (1987)]. A commonly used single step isolation of RNA involves homogenizing cells in 4M guanidinium isothiocyanate, followed by the sequential addition of sodium acetate, pH 4, phenol, and chloroform/ isoamyl alcohol. After centrifugation, RNA is precipitated from the upper layer by the addition of alcohol [P. Chomczynski and N. Sacchi, *Anal. Biochem.*, 162:156–159 (1987) and "Preparation and Analysis of RNA" in *Current Protocols in Molecular Biology*, Unit 4.2 (Supplement 14), ed. F. M. Ausubel et al, John Wiley, (1991)]. Less commonly used methods include the addition of hot phenol to a cell suspension, followed by alcohol precipitation [T. Maniatis et al, *Molecular Cloning, A Laboratory Manual*, Cold Spring Harbor Laboratory (1982)]; the use of anionic or non-ionic surfactants to lyse cells and liberate cytoplasmic RNA; and the use of inhibitors of RNases such as vanadyl riboside complexes and diethylpyrocarbonate [L. G. Davis et al, "Guanidine Isothiocyanate Preparation of Total RNA" and "RNA Preparation: Mini Method" in *Basic Methods in Molecular Biology*, Elsevier, N.Y., pp. 130–138 (1991). U.S. Pat. No. 4,843,155, Chomczynski, describes a method in which a stable mixture of phenol and guanidinium salt at an acidic pH is added to the cells. After phase separation with chloroform, the RNA in the aqueous phase is recovered by precipitation with an alcohol.

The ability of cationic surfactants to lyse cells and simultaneously precipitate RNA and DNA from solution was described in U.S. Pat. No. 5,010,183, by Macfarlane. The −183 patent's method differs fundamentally from those described above in that its first step renders the RNA insoluble, whereas in the above described methods the first step is to solubilize RNA. In the preferred method of the '183 patent, a 2% solution of the surfactant benzyldimethyl-n-hexadecylammonium chloride together with 40% urea and other additives is added to a cell suspension, and the mixture is centrifuged. The pellet is resuspended in ethanol, from which the RNA and DNA is precipitated by the addition of a salt. In attempts to apply this method to blood, the inventor found that the use of the latter surfactant and other commercially available surfactants results in inefficient precipitation of RNA and incomplete lysis of blood cells [see Tables I and II, below]. There is a need for improved cationic surfactants for this purpose.

Current methods for analyzing RNA in blood use amplification methods (including the polymerase chain reaction), and are capable of detecting the presence of specific sequences of RNA present in minute amounts. Investigators wishing to study RNA in white blood cells are likely to separate these cells from blood by centrifugal methods (typically through a gradient of Ficoll/hypaque), and then apply one of the above described methods to the isolated cells. Thus, there is no established method for isolating RNA from whole blood. Similarly, investigators wishing to study viruses may separate viral RNA from plasma using such methods.

Even in view of these known methods, the use of RNA in clinical practice is hampered by the difficulty of separating RNA from the protein and DNA in the cell before the RNA is degraded by nucleases, such as RNase. RNase and other nucleases are present in blood in sufficient quantities to destroy unprotected RNA in a few seconds. Successful methods for the isolation of RNA from cells must be capable of preventing hydrolysis of RNA by nucleases.

There remains a need in the art for a simple method for isolating RNA from blood, other fluids and cells, which method minimizes hydrolysis and degradation of the RNA so that isolated RNA can be used in clinical studies.

SUMMARY OF THE INVENTION

In one aspect, the present invention provides a novel method for isolating RNA from a biological sample, including blood, involving the use of an aqueous, cationic surfactant solution comprising a selected quaternary amine. The selected quaternary amine is produced through the reaction of a quaternary amine hydroxide and an acid of the group consisting of phosphoric, sulfuric, formic, acetic, propionic, oxalic, malonic, succinic and citric. Preferably, the quaternary amine is either an acyltrimethylammonium or an acylbenzyldimethylammonium, where the acyl group contains 12, 14, 16 or 18 carbons.

In another aspect, the invention provides a kit for isolating and purifying RNA from a biological sample which contains at least an aqueous surfactant as described herein.

In still another aspect, the present invention provides a novel surfactant solution useful for extracting RNA from biological samples which comprises a selected quaternary amine salt produced by the reaction of a quaternary amine hydroxide and an acid selected from the group consisting of phosphoric, sulfuric, formic, acetic, propionic, oxalic, malonic, succinic and citric.

Other aspects and advantages of the present invention are described further in the following detailed description of the preferred embodiments thereof.

DETAILED DESCRIPTION OF THE INVENTION

The present invention provides a method for isolating RNA from biological samples which uses a selected novel cationic surfactant comprising a selected quaternary amine, and which method is characterized by significant advantages over methods of the prior art.

1. The Surfactants of the Invention

The novel quaternary amine surfactants of this invention are characterized by the formula below:

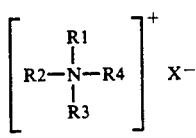

Formula I wherein R1 through R4 are independently selected from an alkyl chain containing from the 1 to 20 carbons, and an aryl group containing from 6 to 26 carbons. Suitable aryl groups are phenyl, lower alkyl-substitute benzyl, and/or halogenated benzyl. Presently preferred anions, i.e., the $X^-$ of Formula I, of the quaternary amine surfactants are phosphate, sulfate, formate, acetate, propionate, oxalate, malonate, succinate and citrate.

Presently preferred quaternary amine surfactants for use in the RNA isolation method of this invention include the oxalate, malonate and succinate salts of acyltrimethylammonium in which the acyl group is 12, 14 or 16 carbons in length. A presently most preferred surfactant is the oxalate salt of acyltrimethylammonium, wherein the acyl group is 14 carbons in length. Other preferred quaternary amine surfactants for such use include the sulfate, phosphate, formate, acetate and propionate salts of acylbenzyldimethylammonium in which the acyl group is 12, 14, 16 or 18 carbons in length. The surfactants of Formula I, which are characterized by the formate, acetate and phosphate salts of hexadecylbenzyldimethylammonium are also desirable.

A novel cationic surfactant useful in the method of the present invention can be obtained as follows: A commercially available surfactant halide in water at about 5 to 30% weight by volume is used as the starting material. Preferably the surfactant halide is at about 15% wt/v in water. A number of commercially available quaternary ammonium halides are available for this purpose from Sigma Chemical Co., including, for example, tetradecyltrimethylammonium bromide.

The surfactant halide is converted to the hydroxide by passing through an anion exchange resin prepared in the hydroxide form, such as Dowex 1 (Sigma Chemical). When the quaternary ammonium halide is passed through this column chromatography step, hydroxyl groups on the resin are exchanged for the halide ion. The resulting surfactant hydroxide, such as tetradecyltrimethylammonium hydroxide, is assayed by titration. The quaternary ammonium hydroxide is then combined with, and neutralized by, the addition of an acid selected from the group consisting of phosphoric, sulfuric, formic, acetic, propionic, oxalic, malonic, succinic and citric. One of skill in the art can readily adjust the amount of the selected acid to acheive neutralization. The resulting quaternary amine surfactant has the formula represented above.

For use in the method of the present invention in isolating RNA, the novel surfactants are in an aqueous solution at a concentration of about 0.01 to 0.2 molar at a pH of between 4 and 8. Alternatively, especially when acylbenzyldimethylammonium salts are used as the quaternary amine surfactant in the method of RNA isolation, it is advantageous to add 50 mM excess acid.

A particularly desirable novel surfactant solution of Formula I for use in the method described below is also characterized as follows. The surfactant solution is not excessively viscous, i.e., less than 2 cp. The surfactant solution does not crystallize under typical storage conditions, i.e., temperatures of about 0 to 30 C. and storage times of about one month. Further, when the surfactant is added to blood in the process of RNA isolation described below, and the mixture is centrifuged, the resulting pellet is of small volume relative to the volume of the blood used in the method, and not dark in color. Additionally, the pellet contains a substantial proportion, that is, greater than about 30%, of RNA endogenously present in blood or added to the surfactant simultaneously with the blood. The pellet does not contain substances, such as hemoglobin or its derivatives, which, after extraction with formamide and precipitation with salt or passage through a chromatography column, tend to inhibit the action of the reverse transcriptase, DNA polymerase, or other enzymes used in the detection of RNA.

Using the criteria listed above, those skilled in the art will be able to obtain a variety of useful novel surfactants of Formula I for the practice of the RNA isolation method of this invention. It is anticipated that these novel surfactants of Formula I may have other uses common to surfactants in general, which uses are readily apparent to one of skill in the art.

2. The RNA Isolation Method of the Invention

In the method of the invention, a biological sample is mixed with a selected cationic surfactant solution of the invention as described above. Contact of the sample with the surfactant according to this method, causes substantially simultaneous lysis of the cells in the sample and precipitation of the RNA in a complex with the surfactant from the lysed cells. The precipitated RNA is preferably extracted from the pellet by either a chaotropic salt and optional phenol extraction, or by a formamide buffer, and further isolated by alcohol precipitation or column chromatography. This method is discussed in more detail below.

As used throughout this specification, the term "biological sample" includes whole blood, plasma, serum, urine, tissue, cells, and other body fluids. As used herein, "RNA" includes transfer (t) RNA, ribosomal (r) RNA, and messenger (m) RNA.

The method of this invention provides a faster and more convenient method for extracting RNA from biological samples, particularly blood. The method of this invention is rapid; it is possible for the whole procedure to be completed in an hour or less. Significantly, the RNA obtained by the method, particularly from blood, is of an adequate purity such that it is useful for clinical or other uses, such as the use of reverse transcriptase followed by the polymerase chain reaction. Advantageously, it is not necessary to isolate cells prior to use of this method and only simple equipment is required for performance of the method. After the sample is combined with the surfactant of the invention, the combination can be transported to the laboratory for use in clinical or other analysis without extensive degradation of the RNA.

The method of the present invention relies for its efficacy on the use of the novel cationic surfactants identified above. As demonstrated in the examples below, these novel surfactants are unexpectedly efficient in lysing blood and other fluids and tissues containing intact cells and unexpectedly efficient in precipitating RNA. They are also stable on storage, in that they do not precipitate from aqueous solution.

In the practice of the present invention, a selected biological sample, e.g., blood, is mixed rapidly with a solution of a selected novel cationic surfactant described herein. Generally, in the mixture, 5 to 40 volumes of blood per 100 volumes of surfactant solution are used. The blood and surfactant may be in contact in the mixture for between about 5 minutes to about 24 hours. Presently, a contact time of about 10 minutes is used. No other processing is needed. In this mixture, the quaternary amine surfactant forms an insoluble ionic complex, characterized by hydrophobic binding of the surfactant tails, with the nucleic acids (both DNA and RNA) in the sample.

After the formation of the complex for the selected time, the surfactant/nucleic acid complex is separated from the mixture. In a preferred embodiment of this separation step, the blood-surfactant mixture is centrifuged to precipitate the surfactant/nucleic acid complex. This can conveniently be performed in about 5 to about 30 minutes at about 5000 to about 100,000 g, using about 1 ml samples in an Eppendorf microcentrifuge. When blood is the sample, presently preferred conditions are about 5 minutes at about 16,000 g, although any approximately equivalent centrifugation could be used. If the sample is cultured cells, lesser centrifugation times and speeds may be desirable. One of skill in the art can determine the appropriate centrifugation depending on the nature of the biological sample. A suitable alternative to centrifugation is filtration using a filter of about 0.22 micron.

After the separation step, the supernatant is removed, and the resulting pellet (or filtrate), which comprises the surfactant/nucleic acid complex is optionally washed with water. The pellet (or filtrate) is then extracted to solubilize the RNA and dissociate it from its complex with the surfactant. In one embodiment of the dissociation step of the method of the invention, a concentrated salt solution is used to extract the RNA from the surfactant/RNA complex. Typically, a desirable concentration of salt for this purpose is in excess of 800 mM in about one-fifth the volume of the surfactant. It is also advantageous to use salts which inhibit RNases. A particularly suitable salt solution for this purpose includes 4M guanidinium isothiocyanate with 100 mM sodium acetate buffer, at about pH 4. However, other suitable salt solutions could be used in this step, provided that the salt is added in sufficient concentration to dissociate the RNA/surfactant complex. One of skill in the art may select other salts at desired concentrations for this purpose.

In another embodiment, the separation step may be followed by an alternative step for dissociating the RNA from the nucleotide/surfactant complex. In this method, an extracting solvent consisting primarily of formamide, preferably buffered with a suitable salt and acid, may be used to treat the pellet resulting from the separation step described above. A preferred solvent useful for extracting RNA from the surfactant/nucleotide pellet is optimally formamide containing 0–8% w/v sodium acetate or ammonium acetate and 0–1% v/v acetic acid. More preferred is formamide with 4% w/v of the salt and 0.16% v/v acid. The presence of the salt and acid may inhibit RNases. The extraction is carried out at about 25° C. to about 100° C. for a time period from about 5 to about 30 minutes with occasional vortexing. Presently preferred conditions are 80° C. for about 10 minutes with occasional vortexing. Selection of the specific conditions for this step may readily be performed by one of skill in the art.

Extraction of the pellet with hot formamide containing a salt unexpectedly results in the preferential extraction of RNA. The addition of the salt with the formamide is also convenient, because the subsequent addition of ethanol described below results in the precipitation of RNA.

The quality and quantity of the extracted RNA is also enhanced by the optional addition of an RNase inhibitor, such as aurin tricarboxylic acid (0.5–5 mM) or diethylpyrocarbonate, to the extracting solvent. Other inhibitors of RNase may be selected for this purpose by one of ordinary skill in the art.

At the completion of this extraction, the mixture is optionally centrifuged at rates the same or similar to those indicated above. The supernatant is added to an equal volume of ethanol, and the mixture is cooled to −20° C. or below. Thereafter the RNA is centrifuged into a pellet and processed by conventional methods.

An alternative to this ethanol precipitation step is to pass the formamide extract containing the RNA through a size exclusion column, such as Trisacryl GF-05, using conventional flow, spin-column or push column techniques. The RNA emerges from the column in the buffer with which the column was equilibrated.

Regardless of which embodiment of the method is employed to dissociate the RNA from its complex with the quaternary amine surfactant, the resulting RNA can be optionally further purified according to this method by phenol/chloroform extraction and precipitated by the addition of ethanol or isopropanol in conventional methods as described by Maniatis et al, and Wallace, both cited above, or by column chromatography.

3. A Kit of the Invention

One or more of the above-described surfactant solutions may be readily prepared in a kit for isolating ribonucleic acid from a biological sample. A presently preferred surfactant for such use is acyltrimethylammonim oxalate, with 14 carbons in the acyl group. Additional components of such a kit would include the reagents and containers necessary for the performance of the separating and dissociating steps of this method, i.e., the formamide solvent and/or the guanidinium isothiocyante solution. Optionally the reagents for accomplishing the additional purification steps identified above may also be included in such a kit for ready performance of this method. Other conventional components of kits for such isolation methods may also be included in a kit.

The following examples illustrate the preferred methods for performing the method of the invention. These examples are illustrative only and do not limit the scope of the invention.

EXAMPLE 1

Synthesis of a Surfactant for Use in the Method

A surfactant useful in this invention is synthesized as follows. A 15% w/v solution of tetradecyltrimethylammonium bromide (Sigma Chemical Corp.) is dissolved in water at 50° C. This solution is passed through an ion exchange resin (Biorad 1 TM, Sigma) in the hydroxide form, bed volume equal to applied volume. In this column, the bromide ions of the quaternary ammonium salt are exchanged for hydroxide ions. The effluent containing the resulting aqueous surfactant hydroxide is collected, and a diluted sample is titrated to neutrality with dilute HCl to determine its concentration.

The surfactant hydroxide is then neutralized with 0.5M oxalic acid. The mixture is diluted to give a 0.1M solution with respect to the surfactant, and with neutral reaction. The result is a faintly opalescent, colorless aqueous solution of a desired surfactant for use in this invention, tetradecyltrimethylammonium oxalate, which foams on shaking.

EXAMPLE 2

Synthesis of Additional Surfactants

Other surfactants useful in this invention are synthesized as described in Example 1, except that the identities of the quaternary ammonium ion and acid differ as indicated.

Acyltrimethylammonium with R1 being acyl of 12, 14, or 16 carbons in length and R2, R3 and R4 being methyl (purchased as bromide salts from Sigma), or a acylbenzyldimethylammonium with R1 being acyl of 12, 14, 16, or 18 carbons in length, R2 being benzyl, and R3 and R4 being methyl (purchased as chloride salts from Aldrich) were employed. As described in Example 1, an aqueous solution of each quaternary ammonium salt was passed through an ion exchange column and the surfactant hydroxide obtained. Each hydroxide was neutralized with an acid selected from the group hydrobromic, hydrochloric, phosphoric, sulfuric, formic, acetic, propionic, oxalic, malonic, succinic and citric, so that the counter ion, X was bromide, chloride, phosphate, sulfate, formate, acetate, propionate, oxalate, malonate, succinate and citrate in individual surfactants.

These aqueous surfactants were then used in experiments to obtain RNA from blood as described in Example 3.

EXAMPLE 3

Lysis of Blood by Surfactants

The ability of the novel surfactants to lyse blood to a useful extent for the practice of the invention is illustrated by the following experiment.

Surfactant solutions synthesized as described in Example 2 (1 ml) were placed in Eppendorf microcentrifuge tubes. Two hundred microliters of blood anticoagulated with 1/10 vol 3.2% sodium citrate was added with immediate mixing. The mixture was centrifuged at 16,000 g for 5 minutes, and the supernatant was removed by aspiration.

The resulting pellet was examined visually and graded. The results are provided in the following table, where 12, 14, or 16-TMA indicates acyltrimethylammonium with acyl of 12, 14, or 16 carbons in length, and 12, 14, 16, or 18-BA indicates acylbenzyldimethylammonium with acyl of 12, 14, 16, or 18 carbons in length. The counter ions of the surfactants are indicated along the left side of the table.

The pellets were graded using the following numerical scale, which is reported in Table I:

0 = pellet almost invisible to the unaided eye;
1 = lightly colored pellet or smear of material on side of tube with minimal volume;
2 = brown pellet 2-3 mm in long axis, incompletely covering the bottom of the tube;
3 = brown pellet 3-4 mm in long axis, completely covering bottom of tube;
4 = dark brown, 4-5 mm in long axis;
5 = greater than 5 mm in long axis.

Pellets with scores of 0 or 1 contain small amounts of material other than RNA and DNA. Pellets with higher scores contain unacceptably high amounts of contaminating material, presumably including hemoglobin or a denatured form of hemoglobin.

In those cases in which the surfactant tended to crystallize from solution on standing or storage at 4° C., the result is given in parentheses.

TABLE I

| | Size of Pellet | | | | | | |
| | Cationic Surfactant | | | | | | |
| Ion (X$^-$) | 12-TMA | 14-TMA | 16-TMA | 12-BA | 14-BA | 16-BA | 18-BA |
|---|---|---|---|---|---|---|---|
| Bromide | 2 | 2 | 2 | | | | |
| Chloride | 1 | 2 | 1 | 2 | 2 | (2) | (5) |
| Phosphate | 2 | 2 | 1 | 2 | 1 | (1) | (1) |
| Sulfate | 0 | 1 | 1 | 2 | 2 | 2 | (2) |
| Formate | 3 | 0 | 2 | 1 | 0 | (0) | 1 |
| Acetate | 0 | 0 | 1 | 0 | 0 | (0) | 1 |
| Propionate | 3 | 0 | 2 | 1 | 0 | 0 | 0 |
| Oxalate | 1 | 1 | 1 | 3 | 3 | 3 | (2) |
| Malonate | 0 | 1 | 1 | 3 | 3 | 2 | (2) |
| Succinate | 1 | 1 | 1 | 3 | 3 | (2) | (2) |
| Citrate | | 3 | 3 | | | | |

It can be seen that there is a variation in the efficacy with which cationic surfactants lyse blood cells. Unexpectedly, the dicarboxylic acid salts of acyltrimethylammonium and the monocarboxylic acid salts of acylbenzyldimethylammonium result in smaller pellets. Surprisingly, the length of the acyl chain has little influence on the ability of the cationic surfactant to lyse blood.

EXAMPLE 4

Precipitation of RNA from whole blood by surfactants

In order to examine the efficiency with which the cationic surfactants precipitate RNA, blood (200 microliters, anticoagulated with citrate), was added to 1 ml of the indicated surfactant (0.1M), together with 50 microliters phosphate-buffered saline containing 10 micrograms tRNA as carrier and 20,000 cpm $^{32}$P-RNA (a 2000 base transcript). One hour later, the mixture was centrifuged (16,000 g, 5 minutes), and the supernatant was aspirated and discarded. The radioactivity present in the pellet was then estimated by scintillation counting, and is expressed as a percentage of the radioactivity added. The results are reported in Table II below, wherein the quaternary salts and ions are represented as in Table I. Precipitation of 95% or more of the RNA is thought to be acceptable. Values reported as 101 or 102% are within pipetting error of 100%.

TABLE II

| | Radioactivity of the Pellets (percent) | | | | | | |
|---|---|---|---|---|---|---|---|
| | 12-TMA | 14-TMA | 16-TMA | 12-BA | 14-BA | 16-BA | 18-BA |
| Bromide | 91 | 88 | 79 | | | | |
| Chloride | 95 | 96 | 70 | 77 | 78 | 68 | 57 |
| Phosphate | 94 | 95 | 87 | 86 | 86 | 94 | 88 |
| Sulfate | 101 | 102 | 100 | 76 | 82 | 83 | 87 |
| Formate | 44 | 28 | 80 | 33 | 40 | 94 | 86 |
| Acetate | 15 | 30 | 32 | 33 | 31 | 90 | 76 |
| Propionate | 68 | 24 | 82 | 24 | 30 | 66 | 70 |
| Oxalate | 102 | 99 | 101 | 85 | 75 | 72 | 68 |
| Malonate | 102 | 92 | 93 | 95 | 94 | 80 | 87 |
| Succinate | 100 | 91 | 91 | 93 | 90 | 82 | 89 |

It can be seen that there is a wide variation in the efficiency with which the surfactants precipitate RNA. The most efficacious were salts of acyltrimethylammonium and divalent acids. This result was unexpected. In contrast, the length of the acyl side chain was of lesser import.

EXAMPLE 5

Isolation and Extraction of RNA from whole blood

Samples of blood (100 microliters and 400 microliters) were added to 800 microliters 14-TMA oxalate prepared as in Example 1 in an Eppendorf tube with immediate mixing. The mixture was incubated at room temperature for 0, 15 minutes, 30 minutes or 1 hour before centrifugation (5 minutes at 16,000 g). The supernatant was aspirated and the pellet was washed briefly with RNase-free water.

The pellet was then extracted with an extracting buffer, produced by mixing 4 grams sodium acetate and 0.16 mL acetic acid with 100 ml formamide, by heating at 80° C. for 10 minutes with occasional vortexing. The mixture was centrifuged (16,000 g, 5 minutes), and the supernatant was added to 400 microliters ethanol and cooled to −80° C. for 10 minutes. The precipitated RNA was harvested by centrifugation (16,000 g, 5 minutes), dissolved in a formaldehyde sample buffer and electrophoresed in agarose by a conventional technique.

Examination of the gel under ultraviolet light after staining with ethidium bromide showed the presence of rRNA and other RNA in the lanes loaded with the 100 microliter samples of blood. The lanes loaded with 400 microliters blood revealed RNA that was partially degraded. There was no difference between the lanes containing samples incubated with the surfactant for 0, 15 minutes, 30 minutes, or 1 hour.

In similar experiments, RNA was isolated from blood using the surfactants listed in Example 3 with pellet scores of 0 or 1. Yields with the benzalkonium surfactants were generally lower than with the alkyltrimethylammonium surfactants. The reason for this is not clear.

EXAMPLE 6

RNA Isolation and Extraction from a Cell Suspension

One hundred thousand HL-60 [ATCC CCL 240] or K562 [ATCC CCL 243] human leukemia cells in 100 microliters were added to 1 ml 100 mM 14-TMA oxalate and centrifuged (16,000 g, 5 minutes). The pellet was extracted and analyzed as described in Example 5. Characteristic bands of rRNA were seen on the gel, as well as other RNA species. This demonstrates that TMA oxalate can be used to isolate RNA from cultured cells.

EXAMPLE 7

RNA Isolation Using Cationic Surfactant and Dithiothreitol

Samples of blood (100 or 200 microliters) were added to 1.0 ml 14-TMA oxalate with or without 10 or 100 mM dithiothreitol, and after centrifugation the pellet was extracted as described in Example 6 with formamide containing 0, 10 or 100 mM dithiothreitol. The RNA was precipitated with ethanol and examined by agarose gel electrophoresis.

The best yield of undegraded RNA was obtained when 100 mM dithiothreitol was added to both surfactant and formamide extracting buffer. Dithiothreitol may increase yields by inhibiting RNase.

EXAMPLE 8

RNA Isolation Using Cationic Surfactant and Aurin Tricarboxylic Acid

An experiment similar to Example 7 was performed using 0, 0.5 or 5 mM aurin tricarboxylic acid (Sigma) in place of dithiothreitol. The best yield of undegraded RNA was obtained when 5 mM aurin tricarboxylic acid was added to the formamide extracting buffer. Aurin tricarboxylic acid is known to inhibit RNase.

EXAMPLE 9

Purification of Extracted RNA Using Column Chromatography

An experiment similar to Example 8 was performed in which blood and radioactive RNA was added simultaneously to the surfactant, except that the formamide extract of the RNA was chromatographed on one of several size exclusion columns pre-equilibrated with an aqueous buffer (Sephadex G50½ or Trisacryl GF-05½) and eluted by gravity feed, centrifugation or by air pressure. The radioactive fraction emerging from the column eluted with air pressure was analyzed by agarose gel electrophoresis which revealed bands of undegraded rRNA. This experiment reveals that RNA can be recovered from formamide by column chromatography.

EXAMPLE 10

RNA Extraction with Guanidinium Isothiocyanate

Samples of blood (50–400 microliters) were added to 1 ml 14-TMA oxalate solution, and centrifuged at 16,000 g for 5 minutes). The resulting pellets were extracted with 100 microliters of an aqueous solution containing 4M guanidinium isothiocyanate and 200 mM sodium acetate buffer, pH 4 by incubation at room temperature for 10 minutes with occasional vortexing. An equal volume of a 1:1 mixture of water-equilibrated phenol and chloroform was then added, and emulsified by vortexing. The phases were separated by brief centrifugation (16,000 g, 2 minutes), and the upper aqueous layer was removed, and added to an equal volume of isopropanol.

After cooling to −20° C. for 30 minutes, the precipitated RNA was harvested by centrifugation (16,000 g, 5 minutes), washed with ethanol, and redissolved for analysis by agarose gel electrophoresis. This revealed the characteristic ethidium bromide stainable bands of cellular RNA. This experiment shows that RNA can be extracted from the surfactant nucleic acid pellet by high salt concentrations. Guanidinium isothiocyanate is known to inhibit RNase, which action may facilitate the recovery of RNA.

EXAMPLE 11

Isolation of Oncogene RNA Using Cationic Surfactant and Formamide Extraction Chronic myelogenous leukemia cells express an oncogene (bcr/abl) which is a hybrid of two genes juxtaposed by a reciprocal translocation between two chromosomes. This oncogene is not expressed in normal cells, but is expressed in the immortal leukemic cell line K562 [ATCC CCL 243]. To demonstrate the utility of the invention in the isolation of RNA for the detection of RNA species by reverse transcriptase and polymerase chain reaction (PCR), 30–10,000 K562 cells were mixed with 200 microliters whole blood, and the RNA was extracted using the method described in Example 5.

The analysis of the resulting RNA was carried out using PCR primers described by Sawyers et al, *Proc. Natl. Acad. Sci. USA*, 87:563–567 (1990). Briefly stated, the isolated RNA was resuspended, and the cDNA was made by incubating it at 37° C. for 1 hour with 200 units Maloney murine leukemia virus reverse transcriptase (BRL, Bethesda, Md.) in a 40 microliters volume with 20 units RNasin, 5 mM dithiothreitol, 20 pmol primer B (5'-TCAGACCCTGAGGCTCAAAGTC-3'), [SEQ ID NO: 1] 1 mM deoxynucleotide triphosphates (Pharmacia), in a PCR buffer (50 mM KCl; 4 mM MgCl$_2$; 50 mM TRIS pH 8.4; 100 mg/ml bovine serum albumin). The reaction was stopped by heating to 95° C. 80 microliters of PCR buffer and 20 pmol of primer A (5'-GAAGCTTCTCCCTGGCATCCGT-3') [SEQ ID NO: 2] was added. The mixture was overlaid with 100 microliters mineral oil and programmed to cycle. All procedures were modified from those published by using the "hot-start" technique.

The Thermal Cycler (Perkin Elmer-Cetus, Emeryville, Calif.) was programmed as follows: denature at 95° C. for 30 seconds, anneal at 55° C. for 30 seconds and extend at 72° C. for 1 minute when primers A and B were used. PCR products were analyzed on 1% agarose gels with ethidium bromide.

Examination of the resulting gel of such an experiment under ultraviolet light revealed the amplification of a 179 base pair fragment from the blood samples containing 1000 or 200 K562 cells in the 200 microliter sample of blood. No amplified product was detected in a control sample from which reverse transcriptase was omitted.

In other similar experiments, amplification of the bcr/abl oncogene was obtained using other surfactants to precipitate the RNA from the blood, including 16-TMA succinate, 14-BA succinate, 16-BA acetate and 14-BA phosphate, and in samples of RNA extracted from the surfactant/nucleotide pellet by the guanidinium isothiocyanate. This shows that the described cationic-surfactant method for isolating RNA from whole blood yields RNA which is suitable for reverse transcription and amplification by PCR without the necessity of further purification.

EXAMPLE 12

Isolation of Oncogene RNA Using Cationic Surfactant and Guanidinium Isothiocyanate Extraction An experiment similar to Example 11 was performed, except that the guanidinium method of Example 10 was used to isolate the RNA. An amplified product of the appropriate size was seen when RNA from blood samples contained 30 or more K562 cells. This experiment shows that extracting the surfactant nucleotide complex with guanidinium isothiocyanate as described yields RNA which is suitable for amplification without further purification. As described, this method would appear to be capable of detecting less than one leukemic cell per microliter of blood of patients with chronic myelogenous leukemia having the Philadelphia chromosome, and this illustrates the great sensitivity of this method.

Numerous modifications and variations of the of the present invention are included in the above-identified specification and are expected to be obvious to one of skill in the art. Such modifications and alterations to the compositions and processes of the present invention are believed to be encompassed in the scope of the claims appended hereto.

---

What is claimed is:

1. A method for isolating nucleic acids from a biological sample comprising the step of contacting the sample with an aqueous quaternary amine surfactant, wherein said quaternary amine has the formula

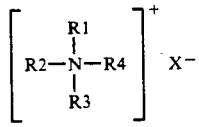

wherein R1 through R4 are independently selected from an alkyl chain containing from the 1 to 20 carbons, and an aryl group containing from 6 to 26 carbons and X− is selected from the group consisting of phosphate, sulfate, formate, acetate, propionate, oxalate, malonate, succinate and citrate.

2. The method according to claim 1 wherein said sample is whole blood.

3. The method according to claim 1 wherein at least one of R1, R2, R3 and R4 is aryl and is selected from the group consisting of phenyl, lower alkyl-substitute benzyl, and halogenated benzyl.

4. The method according to claim 1 wherein said quaternary amine is acyltrimethylammonium, which contains an acyl group of 12, 14, or 16 carbons in length, and X− is selected from the group consisting of oxalate, malonate and succinate.

5. The method according to claim 4 wherein said quaternary amine is acyltrimethylammonium, which contains an acyl group of 14 carbons in length, and X− is oxalate.

6. The method according to claim 3 wherein the quaternary amine is acylbenzyldimethylammonium, the acyl group being 12, 14, 16, or 18 carbons in length, and the acid is selected from the group consisting of sulfuric, phosphoric, formic, acetic, and propionate.

7. The method according to claim 1 further comprising the step of forming an insoluble ionic complex between the nucleic acids, including RNA, in the sample and the surfactant.

8. The method according to claim 7 comprising separating said complex from the solution by centrifuging the sample and surfactant mixture.

9. The method according to claim 7 comprising separating said complex from the solution by filtration.

10. The method according to claim 5 further comprising the step of dissociating the nucleic acids from the nucleic acid/surfactant complex by extracting said complex with an concentrated salt solution.

11. The method according to claim 10 in which said solution comprises 4M guanidinium isothiocyante with 100 mM sodium acetate buffer at about 4 pH.

12. The method according to claim 5 further comprising the step of dissociating the nucleic acids from the complex by extracting the nucleic acids with a formamide solvent optionally buffered with a suitable salt and acid.

13. The method according to claim 12 wherein the salt is sodium acetate or ammonium acetate.

14. The method according to claim 12 wherein said said acid is acetic acid.

15. The method according to claim 1 wherein the biological sample is selected from the group consisting of whole blood, plasma, serum, urine, tissue, and cells.

* * * * *